(12) United States Patent
Briggs et al.

(10) Patent No.: US 7,220,884 B2
(45) Date of Patent: May 22, 2007

(54) HYDROAMINOMETHYLATION OF OLEFINS

(75) Inventors: John R. Briggs, Charleston, WV (US); Gregory T. Whiteker, Charleston, WV (US); Jerzy Klosin, Midland, MI (US)

(73) Assignee: Dow Global Technologies, Inc., Midland, MI (US)

( * ) Notice: Subject to any disclaimer, the term of this patent is extended or adjusted under 35 U.S.C. 154(b) by 136 days.

(21) Appl. No.: 11/040,762

(22) Filed: Jan. 21, 2005

(65) Prior Publication Data

US 2005/0215825 A1    Sep. 29, 2005

Related U.S. Application Data

(60) Provisional application No. 60/565,781, filed on Apr. 27, 2004, provisional application No. 60/543,168, filed on Feb. 10, 2004.

(51) Int. Cl.
*C07C 209/00* (2006.01)
*C07D 265/30* (2006.01)
*C07D 207/06* (2006.01)

(52) U.S. Cl. ............... 564/485; 564/467; 544/178; 548/579

(58) Field of Classification Search ............... 564/467, 564/485; 544/178; 548/579
See application file for complete search history.

(56) References Cited

U.S. PATENT DOCUMENTS

| | | | |
|---|---|---|---|
| 3,513,200 A | 5/1970 | Biale | |
| 4,748,261 A | 5/1988 | Billig et al. | |

FOREIGN PATENT DOCUMENTS

| | | | |
|---|---|---|---|
| DE | 103 21 421 | | 5/2003 |
| GB | 1 468 773 | | 7/1974 |
| WO | WO 96/02508 | | 2/1996 |
| WO | WO 01/64621 A1 | * | 9/2001 |

OTHER PUBLICATIONS

Breit B., "Substrate-Directed Diastereoselective Hydroaminomethylation of Methallyilic Alcohols," Tetrahedron Letters, vol. 39, No. 29, pp. 5163-5166, 1998.

Rische et al., "One-Pot Synthesis of Pharmacologically Active Secondary and Tertiary 1-(3,3-Diarylpropyl)amines via Rhodium-Catalysed Hydroaminomethylation of 1,1-Diarylethenes", Tetrahedron, vol. 55, No. 7, pp. 1915-1920, 1999.

Lin, et al., "Zwitterionic rhodium complex catalzyed hydroaminomethylation of arylethylenes," Tetrahedron Letters, vol. 42, No. 13, pp. 2423-2425, 2001.

Teuma et al., "Tandem Carbonylation Reactions: HYdrolomylation aand Hydroeaminomethylation of alkenes catalyzed by cationic A(H2C(3,5-ME2PZ)2)Rh(CO)LU+Complexes," Organometallics, vol. 22, No. 25, pp. 5261-5267, 2003.

Rische et al., "One-Pot Synthesis of Secondary and Tertiary Napthpropylamines by Rhodium(I)-Catalysed Carbonlative Hydroaminomethylation," Tetrahedron, vol. 55, No. 25, pp. 7841-7846, 1999.

Nagy et al., "Homogeneous catalytic hydroaminomethlatio not steroids with aminoalcohols," Journal of Organometallic Chemistry, vol. 586, No. 1, pp. 101-105, 1999, date unknown.

Liebigs Ann. Chem. 1953, 582, 133-161.

Jones, J. Organomet. Chem. 1989, 366, 403-408.

Tetrahedronl, 1999, 55, 9801-9816.

Beller et al., J. Am. Chem. Soc., 2003, 125, 10311-13018.

Science, 2002, 297, 1676-1678, Seayad et al.

Pruett, J. Org. Chem., 1969, 34, 327.

Van Leeuwen et al., Organometallics, 1995, 14, 34-43.

J. Am. Chem. Soc., 1993, 115, 2066-2068.

Bergmann et al., Tetrahedron, Lett., 1997, 38, 4315-4318.

Angew. Chem. Int. Ed., 2003, 42, 5615-5619.

Gupta, P., P. Tet. Lett., 2003, 44, 4231-4232.

Morita, et al., Tetrahedron 1998, 54, 4811.

* cited by examiner

Primary Examiner—J. Parsa

(57) ABSTRACT

The present invention relates to a method comprising the step of contacting under hydroaminomethylation conditions, an olefin, an amine, a rhodium-phosphorous ligand, and synthesis gas (syngas). In particular, it has been discovered that, under some circumstances, a neutral rhodium-monodentate phosphite ligand is prescribed. The invention provides a simple way of making, in high yields and regiospecificity, a variety of products, including pharmacologically active products such as ibutilide, terfenadine, and fexofenadine, and derivatives thereof.

14 Claims, No Drawings

HYDROAMINOMETHYLATION OF OLEFINS

This application claims the benefit of U.S. Provisional Application No. 60/543,168, filed Feb. 10, 2004 and 60/565,781 filed Apr. 27. 2004.

BACKGROUND OF THE INVENTION

The present invention relates to hydroaminomethylation of olefins. Aliphatic amines are useful in a variety of applications including agrochemical and pharmaceutical products and intermediates, as well as precursors for polymers such as polyurethanes. The homogeneous hydroaminomethylation reaction was reported by Reppe at BASF (*Liebigs Ann. Chem.* 1953, 582, 133–161) using a homogeneous cobalt carbonyl catalyst. This reaction consists of a tandem, one-pot olefin hydroformylation/reductive amination sequence in which the intermediate aldehyde reacts with a primary or secondary amine to form an imine or enamine intermediate, which undergoes hydrogenation to form a secondary or tertiary amine. U.S. Pat. No. 3,513,200 reports the use of a homogeneous rhodium triphenylphosphine catalyst for synthesis of tertiary amines via hydroaminomethylation. The use of hydroaminomethylation with ethylene to form n-propylamines was reported by Jones in *J. Organomet. Chem.* 1989, 366, 403–408. This reaction was completely selective for normal propylamines since ethylene hydroformylation can produce only a single regioisomer of the intermediate priopionaldehyde. Eilbracht et al. reported in *Tetrahedron* 1999, 55, 9801–9816 that pharmacologically active amines can be prepared by hydroaminomethylation using a homogeneous $[Rh(cod)Cl]_2$ catalyst, however this reaction proceeded with low selectivity to the desired branched regioisomer. Beller et al reported in *J. Am. Chem. Soc.* 2003, 125, 10311–10318 that terminal alkenes can undergo hydroaminomethylation with very high selectivity to the linear amine isomer by use of a rhodium catalyst which employs the Xantphos diphosphine ligand. In *Science* 2002, 297, 1676–1678, Seayad et al. describe the preparation of aliphatic amines by reacting an internal olefin (e.g., 2-butene, 2-pentene, or 2-octene) with an amine (e.g., piperidine, dimethyl amine, or di-n-hexylamine) in the presence of syngas, a phosphine ligand, and a cationic procatalyst, $[Rh^+(cycloocta-1,5-diene)_2]$ $[BF_4^-]$ (also known as $[Rh(cod)_2BF_4]$procatalyst). The researchers also tested a monodentate phosphite ligand under the same reaction conditions but discovered poor amine selectivity—and no conversion to the desired linear amine—from which they concluded that "phosphite ligands are less suitable for the desired reaction because of hydrolysis problems encountered in the presence of water and amines." Id. at 1677. This reported shortcoming of phosphite ligands in hydroaminomethylation is significant since rhodium phosphite catalysts are very useful for olefin hydroformylation, the first step of the hydroaminomethylation sequence. Pruett (*J. Org. Chem.* 1969, 34, 327) reported that the homogeneous rhodium triphenylphosphite catalyst gave higher linear selectivity than the rhodium triphenylphosphine. Bulky monodentate phosphite ligands, such as tris(2-tert-butyl-4-methylphenyl)phosphite, were found by van Leeuwen et al (*Organometallics* 1995, 14, 34–43) to give very high hydroformylation rates under mild conditions. Bidentate bisphosphite ligands can give very high selectivity to linear aldehydes from rhodium-catalyzed hydroformylation of terminal olefins. These catalysts are highly tolerant of a wide range of functional groups which makes their application to the synthesis of complex organic molecules possible (*J. Am. Chem. Soc.* 1993, 115, 2066–2068). Intramolecular examples of hydroaminomethylation of unsaturated amines were reported by Bergmann et al. (*Tetrahedron. Lett.* 1997, 38, 4315–4318) using a highly regioselective bisphosphite ligand.

To ensure hydrogenation of the enamine intermediate to the desired amine, Seayad et al. report that "it is desirable to attain a reaction temperature of 120° C." Id. at 1677. On the other hand, in a later publication (*Angew. Chem. Int. Ed.* 2003, 42, 5615–5619) the same research group report the selective preparation of the enamine intermediate using a [Rh(CO)₂(acac)] procatalyst and a phosphine ligand at temperatures in the range of 65° C. to 125° C.

Although alkyl amines can be made with reasonably high yield and selectivity using the method described by Seayad et al., the requirement of high temperatures makes the method suitable only for olefins, amines, catalysts, and products that are stable at these advanced temperatures. Also, long reaction times require extended use of process equipment, which result in increased processing costs. Accordingly, it would be desirable to find a more efficient and effective way of aminomethylating olefins.

SUMMARY OF THE INVENTION

In a first aspect, the present invention is a method comprising the step of contacting under hydroaminomethylation conditions a) an olefin; b) a primary or secondary amine or ammonia; c) a neutral rhodium-monodentate phosphite ligand complex and d) syngas.

In a second aspect, the present invention is a method comprising the step of contacting under hydroaminomethylation conditions a) an olefin of the class $ArXCR=CR_2$; b) a secondary amine; c) a rhodium-phosphorous ligand complex; and d) syngas; wherein Ar is aryl or substituted aryl, each R is independently H, alkyl, cycloalkyl, aryl, aralkyl, substituted alkyl, substituted cycloalkyl, substituted aryl, or a heteroatom containing group, and X is a linking group, with the proviso that when X is —$CH_2$— or —$OCH_2$—, the phosphorous ligand is a phosphite ligand.

DETAILED DESCRIPTION OF THE INVENTION

In a first aspect, the present invention is a method of preparing an alkylamine by contacting, under hydroaminomethylation conditions, an olefin, an amine, a neutral rhodium-mondodentate phosphite ligand complex, and syngas. The olefin can be terminal (e.g., ethylene, propylene, 1-butene, 1-pentene, 4-methyl-1-pentene, 1-hexene, 1-decene, 1-dodecene, vinylcyclohexane, vinyl-terminated polypropylene, allylbenzene, allylphenol, styrene, isobutylene, 2-methyl-1-pentene, methylenecyclohexane, norbornene, α-methylstyrene, α-cyclohexylstyrene, vinylidene-terminated polypropylene, vinylidene-terminated poly(4-methyl-1-pentene)) or internal (e.g., 2-butene, 2-pentene, 2-hexene, 3-hexene, 2-octene, 3-octene, cyclohexene, stilbene, and methyloleate and derivatives thereof). Furthermore the olefin may contain more than one olefinic group (e.g., butadiene, isoprene, piperylene, 1,7-octadiene, allene, norbornadiene, dicylopentadiene, methyl linoleate, methyl linolinate, oleic acid triglyceride, polybutadienes, and polybutadiene-co-styrene), and may also include olefins containing ketones or aldehydes (e.g., tetrahydrobenzaldehyde), which, for the purposes of this invention, are considered to be diolefins.

The amine can be primary (e.g., methylamine, ethylamine, n-propylamine, n-butylamine, isopropylamine, isobutylamine, t-butylamine n-hexylamine, n-hexylamine, n-octylamine, benzylamine, allylamine, 1-phenylethylamine, 2-phenylethylamine, neopentylamine, cyclohexylamine, ethanolamine) or secondary (e.g., dimethylamine, ethylmethylamine, butylmethylamine, di-n-hexylamine, piperidine, pyrrolidene, morpholine, aniline, dibenzylamine, n-methylaniline, diethanolamine, N-methylbenzylamine, N-methylcyclohexylamine, N-methylallylamine, and indole) and may contain more than one amino group (e.g., ethylene diamine, 1,2-diaminopropane, 1,3-diaminopropane, hexamethylene diamine, piperazine, N-methylpiperazine, 1-(2,3-dichlorophenyl)piperazine, 1,4-diaminocyclohexane, hydrazine, and N,N'-dimethylpropanediamine). The amine can also contain one or more non-amine functional groups that do not participate in the reaction (e.g. 3-methylamino-propionitrile). The mole-to-mole ratio of N—H groups of the amine to olefinic groups of the olefin is preferably not less than 0.5:1, more preferably not less than 0.7:1; and most preferably not less than 0.9:1; and preferably not more than 2:1, more preferably not more than 1.5:1 and most preferably not more than 1.1:1. By way of example, three moles of 1-butene can react with one mole of ammonia, two moles of 1-butene can react with one mole of ethylamine, and one mole of 1-butene can react with diethylamine.

The neutral rhodium-monodentate phosphite ligand complex (hereinafter, complex) is conveniently prepared by contacting a neutral rhodium procatalyst with preferably a stoichiometric excess of a monodentate phosphite ligand in the presence of a solvent such as dioxane, THF, cyclohexane, toluene, acetone, or o-xylene. The monodentate phosphite ligand can be characterized by the general formula $P(OR)_3$, where each R is independently a carbon-containing substituent. Monodentate refers to the fact that the ligand contains only one phosphite group. Preferably, each R independently includes an alkyl, aryl, arylalkyl, arylalkoxy, or carbonylaryl group. Examples of representative monodentate phosphites include triphenylphosphite, tris(2,4-di-t-butylphenyl)phosphite, tri-o-tolylphosphite, tri-p-tolylphosphite, trimethylphosphite, triethylphosphite, tri-n-propylphosphite, tri-n-butylphosphite, tri-t-butylphosphite, tri-1-naphthylphosphite, tri-2-naphthylphosphite, 2,2'-biphenolphenylphosphite, 2,2',4,4'-tetra-t-butyl-2,2'-biphenol 2,4-di-t-butylphenylphosphite, and tribenzylphosphite.

The neutral rhodium procatalyst is a rhodium (I) catalyst precursor characterized by having its positive charge balanced by the negative charge of supporting bound ligands. For example, rhodium dicarbonyl acetonylacetate (also known as $[Rh(CO)_2(acac)]$ procatalyst) is a neutral rhodium procatalyst and, therefore, suitable for the method of the first aspect of the present invention, because the acetonylacetate group is a negatively charged species that is chemically bound to the rhodium cation. On the other hand, $[Rh(cod)_2BF_4]$ is a cationic rhodium procatalyst because the tetrafluoroboronate anion is not chemically bound to the rhodium cation.

Other suitable examples of neutral rhodium procatalysts useful in preparing the complex include $[Rh_4(CO)_{12}]$, $[Rh_2(OAc)_4]$, $[Rh(C_2H_4)_2(acac)]$, $[Rh(cyclooctadiene)(acac)]$, $[(Rh(norbornene)_2(acac)]$, $[(Rh(norbornadiene)(acac)]$, and $[Rh(acac)_3]$ procatalysts.

The mole-to-mole ratio of the monodentate phosphite ligand to neutral rhodium catalyst used to make the complex is preferably not less than 2:1, and more preferably not less than a 4:1; and preferably not greater than a 30:1, and more preferably not greater than 20:1 mole-to-mole excess. The olefin and amine are preferably used in stoichiometric excess with respect to the complex. The mole-to-mole ratio of the complex to amino groups of the amine or olefinic groups of the olefin is preferably not greater than 1:500, and more preferably not greater than 1:200, and preferably not less than 1:10, and more preferably not less than 1:40.

The olefin, amine, and complex and optionally solvent are advantageously saturated with a stoichiometric excess of a mixture of CO and $H_2$ (hereinafter, syngas) and heat—and pressure-adjusted for sufficient time to convert the reactants to the desired aminomethylated product. Alternatively, in a mode that can be advantageous for hindered olefins such as 1,1'-disubstituted olefins (e.g. α-cyclohexylstyrene), the amine or ammonia is added sequentially, i.e. after conversion of the olefin to the intermediate product of hydroformylation. The mole-to-mole ratio of $H_2$:CO is application dependent but preferably varies from not less than 1:1, more preferably not less than 1.5:1, and most preferably not less than 1.8:1, and preferably not greater than 4:1, more preferably not greater than 3:1, and most preferably not greater than 2.2:1. Preferably, the reaction is carried out at a pressure of not less than 200 psi (1380 kPa), more preferably not less than 500 psi (3450 kPa), and most preferably not less than 800 psi (5510 kPa); and preferably not more than 3000 psi (20700 kPa), more preferably not more than 2000 psi (13800 kPa), and most preferably not more than 1500 psi (10340 kPa). Preferably, the reaction temperature is maintained at not higher than 140° C., more preferably not higher than 120° C., and most preferably not higher than 100° C.; and preferably not lower than 20° C., more preferably not lower than 40° C., and most preferably not lower than 60° C.

Although the putative reaction of syngas with the complex would presumably form the same product whether a neutral or a cationic rhodium procatalyst were used, the detrimental formation of a strong acid (e.g., $HBF_4$ from $[Rh(cod)_2BF_4]$) from the reaction of syngas and a complex derived from the cationic rhodium procatalyst is believed to inhibit hydrogenation of the enamine intermediate to the aminomethylated product. For this reason, the neutral rhodium procatalyst is the precursor of choice for making the complex.

It has been surprisingly discovered that aminomethylated products can be prepared in high yields, at relatively low temperatures (<100° C.), and in a relatively short period of time (<5 hours).

In a second aspect, the present invention is a method of preparing an aminomethylated product comprising the step of contacting under hydroaminomethylation conditions a) an olefin of the class $ArXCR=CR_2$; b) a secondary amine; c) a rhodium procatalyst; d) a phosphorous-containing ligand; and e) syngas; wherein Ar is aryl or substituted aryl, each R is independently H, alkyl, cycloalkyl, aryl, aralkyl, substituted alkyl, substituted cycloalkyl, substituted aryl, or a heteroatom containing group, such as methoxy, ethoxy, primary amino, secondary amino, and tertiary amino, and X is a linking group, with the proviso that when X is —$CH_2$— or —$OCH_2$—, the phosphorous ligand is a phosphite ligand. As used herein, the term "phosphorous ligand" refers to a phosphorous-containing ligand.

Ar is preferably substituted or unsubstituted phenyl, naphthyl, anthryl, phenanthryl, or heteroaryl, more preferably substituted or unsubstituted phenyl, most preferably substituted phenyl. Examples of preferred substituted phenyl groups include p-Y-phenyl or methanesulfonamidophenyl where Y is $C(CH_3)_2R''$ wherein R'' is methyl, cyano, hydroxymethylene, alkoxymethylene, carbohydroxy, carbomethoxy, carboethoxy, carbobenzyloxy, amido, orthoformate, formyl, 2-oxazoline, or 2-benzoxazole. More preferred substituted phenyl groups include p-t-butylphenyl, p-methanesulfonamidophenyl, or p-(α-carbomethoxy-α'-methyl)ethylphenyl. X is preferably —CHOH, —CHOSi(CH$_3$)$_3$, or —C=O, more preferably, —CHOH.

Although a neutral rhodium procatalyst is preferred for this second aspect, cationic rhodium procatalysts such as [Rh(cod)$_2$BF$_4$], [Rh(cod)$_2$CF$_3$SO$_3$], [Rh(cod)$_2$ PF$_6$], [Rh(cod)$_2$BPh4], [Rh(ethylenediamine)$_3$NO$_3$], [Rh(bipyridyl)$_3$Cl]$_3$, and [Rh(norbornene)$_2$ClO$_4$] may also be used. The phosphorous ligand is preferably a phosphine or a phosphite ligand. If X is —CH$_2$— or —OCH$_2$—, the phosphorous ligand is a phosphite ligand; for all other X, the phosphorous ligand is unlimited. Preferably, X is —CR'OR', C=O, S, or NR—C=O, wherein each R' is independently alkyl, cycloalkyl, aryl, arylalkyl, trialkylsilyl, or H. More preferably, X is —CHOH, —CHOSi(CH$_3$)$_3$, or —C=O; most preferably —CHOH.

Examples of suitable phosphines for this second aspect include 2,2'-bis(diphenylphosphinomethyl)-1,1'-binaphthyl (NAPHOS), 2,2'-bis[di(3,5-trifluoromethylphenyl)phosphinomethyl]-1,1'-binaphthyl (IPHOS), 2,2'-bis[di(4-trifluoromethylphenyl)phosphinomethyl]-1,1'-binaphthyl, and 9,9-dimethyl-4,5-bis(diphenylphosphino)xanthene (XANTPHOS).

Examples of suitable phosphites include monodentate phosphites, as described hereinabove, and polydentate, preferably bidentate, phosphite ligands, examples of which include Ligand 2, illustrated as follows:

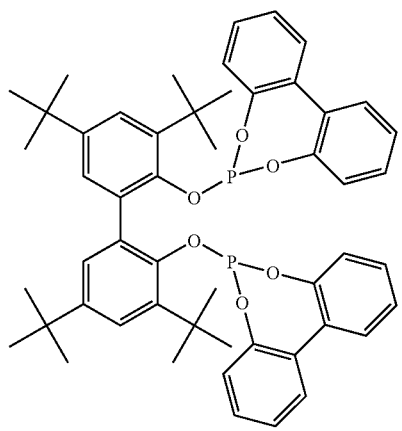

Ligand 2

Other examples of bidentate ligands are disclosed in U.S. Pat. No. 4,748,261, which teachings are incorporated herein by reference.

The process of this second aspect of the present invention provides a simple way of reductively coupling amines and olefins in a single step to make a variety of useful compounds, such as pharmaceutical compounds, including ibutilide, terfenadine, and fexofenadine and derivatives thereof. For such process applications, certain olefin substrates are novel compositions.

The following examples are for illustrative purposes only and are not intended to limit the scope of the invention. Syngas was obtained from Matheson or Airgas and refers to a 2:1 mole-to-mole mixture of H$_2$/CO except where noted otherwise.

EXAMPLE 1

Preparation of Dimethylaminomethylalkane mixture

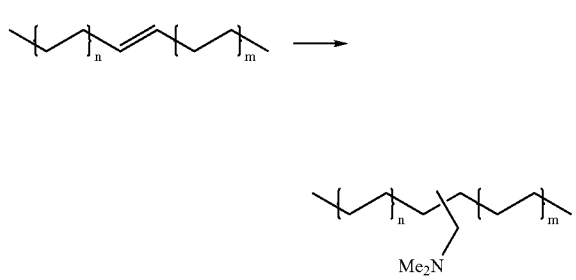

Neodene® Olefin Blend (10/1112/13/12, 319 g, obtained from Shell Chemical) olefin substrate was added to a 1-gal (4-L) reactor in THF (680 g). To this solution was added dimethylamine (222 g), and a solution of a complex prepared from [Rh(CO)$_2$(acac)] (3.7 g) and tris(2,4-di-t-butylphenyl)phosphite (46.2 g, obtained from Aldrich Chemical) in THF (374 g). The final rhodium concentration was about 900 ppm by weight. This mixture was heated to 80° C. and pressurized to 600 psi (4140 kPa) with syngas and stirred under these conditions for 7 hours. The reactor was cooled to 21° C. overnight and the gas phase vented. After stirring under a nitrogen flow for about 1 hour to remove most of the excess dimethylamine, the reactor contents were dumped, stripped of THF and distilled using a Kugelrohr apparatus to yield a colorless mobile liquid (427 g, 99% yield).

EXAMPLE 2

Hydroaminomethylation of Oleic Acid Diethanolamide with Diethanolamine

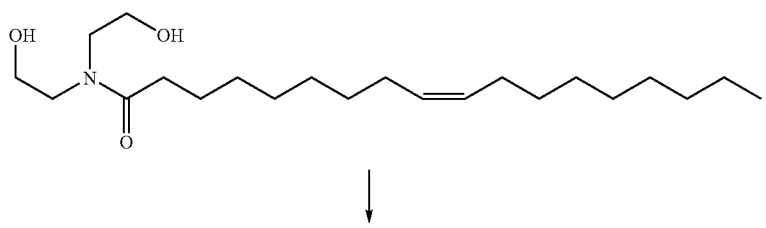

-continued

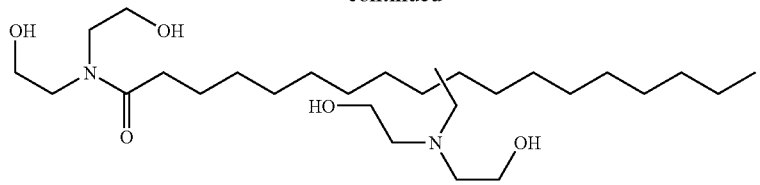

Oleic acid amide (13.49 g), diethanolamine (4.51 g) and THF solvent (20 mL) were added to a nitrogen purged reactor by syringe. The reactor was stirred under ca. 200 psi (1380 kPa) of syngas to saturate the solution. After venting, an aliquot (10.4 g) of a pre-made catalyst solution of [Rh(CO)$_2$(acac)] (5351 ppm by weight Rh) and tris(2,4-di-t-butylphenyl)phosphite ligand (5.00 moles of ligand/mole of Rh) in THF was added to the reactor. The reactor was sealed and pressurized with syngas and heated to 80° C. The pressure was increased to 600 psi (4140 kPa) with additional syngas, and then fed on demand at this pressure throughout the reaction. After 4.5 hours, the reactor was cooled, vented and the reactor contents discharged. The amber solution was extracted with cyclohexane, then toluene, and the supernatent discarded. Acetonitrile was added to the lower brown layer, and stirred briefly. When agitation was ceased, a viscous, honey-colored lower layer was isolated by decantation (16.7 g). H-1 and C-13 NMR spectroscopy showed that the product was the desired with some excess diethanolamine. Mass spectrometry (CI with isobutane) shows a (M+H)$^+$ peak at 489 and a (M+H+Isobutene)$^+$ peak at 545 confirming the molecular weight.

EXAMPLE 3

Hydroaminomethylation of Terminally Unsaturated Isopolypropylene with Dibenzylamine

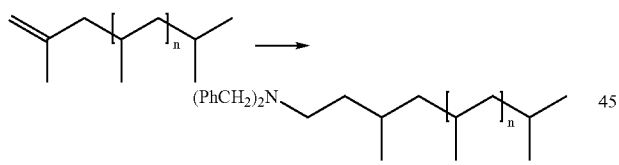

Vinylidene-terminated polypropylene having a weight average molecular weight M$_w$ of about 1800 g/mol (5.43 g, obtained from Baker-Hughes Corporation) was dissolved in toluene (70 mL). A portion of this solution (65 mL) was transferred to a 100 mL Parr reactor, whereupon dibenzylamine (2 mL, 9.8 mmols) and a solution containing complex (20 mL of a stock solution prepared by dissolving [Rh(CO)$_2$(acac)] (2.56 g), 2,4-di-t-butylphenylphosphite (32.09 g), in sufficient THF to give a total solution mass of 200.73 g) was added. The reactor was sealed and pressurized to 600 psi (4140 kPa) of syngas and heated to 80° C. for 130 minutes. After reaction, the pressure was released and the reactor opened while the temperature was still at 60° C., and the contents discharged into a glass beaker. The polymer product was precipitated by addition of methanol (about 2× volume). The solid material was filtered off and washed with methanol until the washings were colorless. The material was dried in vacuo to yield 5.31 grams of product, and was characterized by C-13, and H-1 NMR spectroscopy.

EXAMPLE 4

Hydroaminomethylation of Cyclohexene with Ammonia

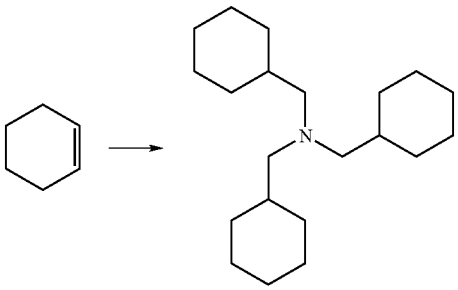

A portion of the stock complex solution as described in Example 3 (10 mL), THF (10 mL) cyclohexene (0.93 g., 11.07 mmols) and ammonia (30 mL of a 0.5 M solution in dioxane) were charged to a 100 ml Parr reactor. The reactor was pressurized with 400 psi (2760 kPa) of syngas and heated to 80° C. for 220 minutes, then cooled and sampled for gas chromatography. The results indicate that 94% of the cyclohexene had been consumed and that the major products were tri(cyclohexylmethyl)amine (90%), di(cyclohexylmethyl)amine (3%) and cyclohexylmethanol (7%).

EXAMPLE 5

Hydroaminomethylation of Ethylidene Norbornene with Morpholine

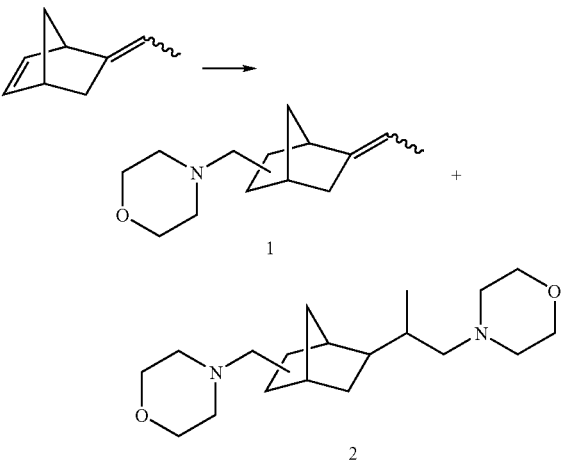

A aliquot (9.81 g) of the stock catalyst solution from example 3 was charged to a 100-mL Parr autoclave along with THF (36.54 g) and morpholine (2.02 g). The reactor was stirred under 200 psi (1380 kPa) of syngas for 15 minutes. The pressure was vented whereupon ethylidene norbornene (0.96 g) was added. The reactor was pressurized to 400 psi (2760 kPa) with syngas and heated to 80° C. for 150 minutes. The reactor was then cooled, and the contents analyzed by gas chromatogaphy/mass spectrometry, which showed that the starting materials had been almost completely converted to a mixture of isomers of mono—and diamines with molecular weights corresponding to the structures 1 (46%) and 2 (54%).

EXAMPLE 6

Hydroaminomethylation of Poly(1,2-butadiene) with Diethanolamine

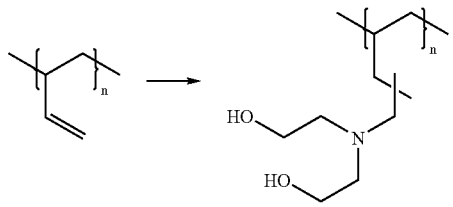

A solution poly(1,2-butadiene) (obtained from Scientific Design Company $M_w$~100,000, 93% vinyl, 7% 1,4-cis, 5.1 weight percent in 50 mL THF) was charged into a 100-mL Parr reactor along with 9.45 g of diethanolamine. The reactor was purged with syngas and vented, whereupon solution of the complex (157.6 g, from a stock complex solution prepared by mixing [Rh(CO)$_2$(acac)] (2.52 g), 2,4-di-t-butylphenylphosphite (31.06 g) in THF (157.6 g)) was added. The reactor was pressurized to 400 psi (2760 kPa) with syngas and heated to 80° C. for almost 4 hours. The reactor was cooled and the contents discharged. The insoluble brown polymer was dissolved in methanol, and reprecipitated with acetone, then recovered by centrifugation and analyzed by H-1 and C-13 NMR spectroscopy to verify that the illustrated product was formed.

EXAMPLE 7

Hydroaminomethylation of Styrene with Morpholine

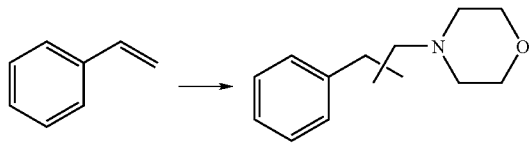

[Rh(CO)$_2$(acac)] (0.1000 g), 2,4-di-t-butylphenylphosphite (1.355 g), tetrahydrofuran (50 mL), morpholine (14.62 g) and styrene (8.81 g) were charged to a 100-mL Parr reactor and then pressurized to 380 psi (2620 kPa) and heated to 80° C. for 4 hours. The reactor was cooled and the contents analyzed by GC mass spectrometry/infrared spectroscopy. The distribution of products was found to be as follows:

| | |
|---|---|
| 2-phenylpropionaldehyde - | 6% |
| 2-phenylpropanol - | 2% |
| 1-morpholino-2-phenylpropane - | 40% |
| 1-morpholino-3-phenylpropane - | 40% |
| 2-phenylpropionaldehyde morpholine enamine - | 10% |
| 1-2/3-dimorpholino-3-phenylpropane - | 2% |

EXAMPLE 8

Hydroaminomethylation of Tetrahydrobenzaldehyde with Morpoholine

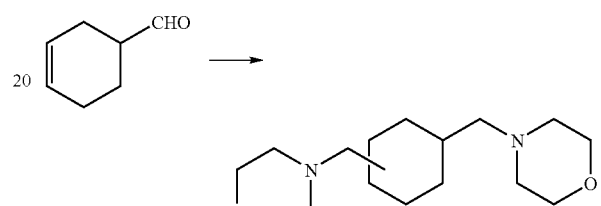

A 100 mL Parr reactor was charged with [Rh(CO)$_2$(acac)] (127.1 mg), Ligand 1 (2.84 g), dioxane (50 mL), hexane (GC internal standard, 1223.5 mg), tetrahydrobenzaldehyde (5.52 g) and morpholine (9.08 g). The reactor was pressurized with 1000 psi (6890 kPa) of 1:1 H$_2$/CO and heated to 90° C. for 4 hours. After 90 minutes, selectivity to diamines was 94%, with no detectable enamine.

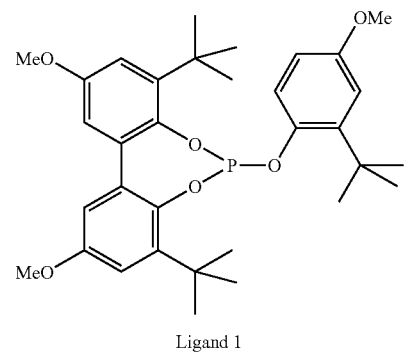

Ligand 1

EXAMPLE 9

Hydroaminomethylation of Polybutadiene with Dimethylamine

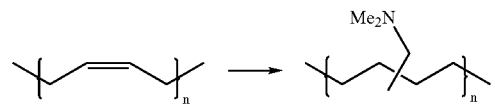

An aliquot (23.31 g) of a stock solution of poly(cis-1,4-butadiene) (19.47 g in 376.1 g of THF) was added to a 100-mL Parr reactor, which was then sealed and pressurized with 300 psi (2070 kPa) of syngas. After venting, solution of complex (9.73 g, from a stock solution of [Rh(CO)$_2$(acac)] (3.0001 g), 2,4-di-t-butylphenylphosphite (37.77 g) and THF (229.2 g)) was added, followed by dimethylamine (3.13 g). The reactor was pressurized to 600 psi (4140 kPa) with syngas then heated to 80° C. After about 135 minutes, the reactor was cooled and the pressure vented. The reactor was opened and the contents transferred to a flask. A solution of 1% by weight of Ionol (antioxidant) was added, but no precipate formed. The solvent was removed in vacuo, and the product was dissolved in ether and precipitated with acetone to give an off white, rubber material. The product was dried in vacuo overnight and characterized by H-1 NMR spectroscopy. The H-1 spectrum showed the almost total absence of olefinic C—H resonances at about 5.4 ppm. New peaks at 2.145 and 2.064 assigned to (CH$_3$)$_2$NCH$_2$— and (CH$_3$)$_2$NCH$_2$— respectively. Additionally, resonances at 1.1–1.6 due to the saturated polymer chain were also present.

EXAMPLE 10

Hydroaminomethylation of Vinylidene-terminated poly(4-methyl-1-pentene) with 3-Aminomethyl-propionitrile A 1 gallon stainless steel autoclave was charged with poly (4-methyl-1-pentene) (76.04 g, 3.5 mmol olefin functionalization, M$_n$ of ~22000), 1.5 L of toluene and 3-aminomethyl-propionitrile (20 mL, 215.6 mmol). The autoclave was pressure tested, briefly purged with N$_2$, purged with syngas (2:1 H$_2$/CO), and the contents stirred under 400 psi syngas (2:1 H$_2$/CO) for 20 min. The reactor was heated slowly to 60° C., vented and charged with a catalyst solution comprising Rh(CO)$_2$(acac) (4.42 g, 17.1 mmol) and tris-2,4-di-t-butylphenylphosphite (23.34 g, 36.1 mmol) in 250 mL toluene via a pressurized (80 psi N$_2$) Whitey cylinder. The reactor was then heated to 80° C., pressurized to 400 psi with syngas (2:1H$_2$/CO) and stirred for 14 h. After cooling to 60° C., the reactor was purged with N$_2$ and dumped. An equal volume of MeOH was added to induce polymer precipitation. The resulting solid was filtered and washed with acetone until the filtrate was colorless (~2 L). The filter cake was dried in a vacuum oven overnight and a sample submitted for $^1$H NMR. Analysis of the NMR data revealed incomplete conversion of the starting material, with 65–70% conversion to desired product. The isolated polymer mixture (vide infra), 68.75 g, was added to the same stainless steel autoclave with an additional 1.5 L of toluene and 3-aminomethyl-propionitrile (20 mL, 215.6 mmol). After purging and stirring under syngas as described above, the reaction mixture was heated to 60° C. and a catalyst solution comprising Rh(CO)$_2$(acac) (4.31 g, 16.7 mmol) and tris-2,4-di-t-butylphenylphosphite (22.99 g, 35.5 mmol) in 250 mL THF was added. The reaction mixture was heated to 80° C., pressurized to 400 psi syngas (2:1 H$_2$/CO) and stirred for an additional 14 h. Isolation of the product as described above yielded 63.58 g of colorless powder. A sample was submitted for $^1$H NMR. Analysis of the NMR data showed that this material was fully converted to the desired aminomethylated product.

EXAMPLE 11

Hydroaminomethylation of α-Cyclohexylstyrene with Piperidine

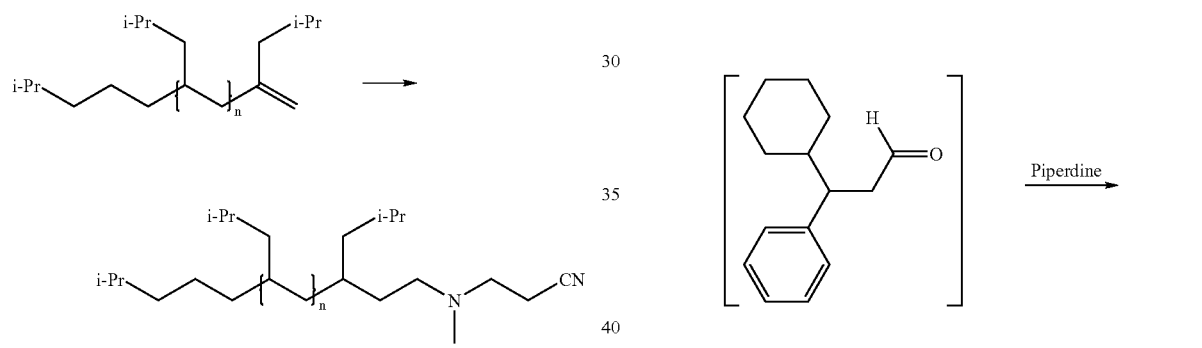

A. Synthesis of α-Cyclohexylstyrene

α-Cyclohexylstyrene was prepared from cyclohexyl phenyl ketone using standard Wittig chemistry (Gupta, P.; Fernandes, R. A.; Kumar, P. *Tet. Lett.* 2003, 44, 4231–4232.) Methyltriphenylphosphonium bromide (29.57 g, 82.77 mmol) was slurried in 600 mL THF in the glovebox. The mixture was cooled to 2° C., and nBuLi (1.6 M in hexanes, 52 mL) was added over 15 min. After 1 h, solid cyclohexyl phenyl ketone (15.18 g, 80.63 mmol) was added, and the solution was allowed to slowly warm to room temperature overnight. Water (200 mL) was added. The solution was extracted with Et$_2$O (3×150 mL). The combined organic extracts were washed with brine, dried (MgSO$_4$) and evaporated under vacuum to give a tan liquid. Ph$_3$PO crystallized upon standing and was removed by filtration and washed with hexane (200 mL). The hexane solution was filtered through a 2 in column of neutral alumina, washing with an additional 200 mL of hexane. The filtrate was evaporated to a colorless liquid which was distilled (46–49° C./0.1 mm Hg) to give 13.72 g of colorless liquid (89% yield).

B. General Hydroformylation Procedure

Hydroformylation solutions were prepared by addition of ligand and $Rh(CO)_2(acac)$ stock solutions to THF solvent followed by addition of olefin solution. Total amount of liquids in each reactor cell was 4 mL. Ligand solutions (0.11 M for monodentate ligands) and $Rh(CO)_2(acac)$ (0.05 M) were prepared in the dry box by dissolving appropriate amount of compound in toluene at room temperature. The olefin solution was prepared by mixing 2.3493 g of α-cyclohexylstyrene and 0.6444 g of dodecane (as a GC internal standard) (1:0.3 molar ratio). Hydroformylation reactions were conducted in an Argonaut Endeavor® reactor system housed in an inert atmosphere glove box. The reactor system consists of eight parallel, mechanically stirred pressure reactors with individual temperature and pressure controls. Upon charging the catalyst solutions, the reactors were pressurized with syn gas ($CO:H_2$—1:1) and then heated to the desired temperature while stirring at 800 rpm. The runs were stopped after 16 hrs by venting the system. Upon opening the reactor 0.1 mL of each reaction mixture was taken out and diluted with 1.6 mL of toluene, and this solution was analyzed by gas chromatography. All GC analyses were performed on DB-5 column using the following temperature program: 100° C. for 5 min, then 10° C./min to 250° C. and then hold for 5 min.

C. Hydroaminomethylation with Sequential Addition of Piperidine

The reactor was charged with 0.085 mL of 0.05 M solution of $Rh(CO)_2(acac)$ and 0.085 mL of 0.11 M solution of Doverphos (Ligand: Rh ratio of 2.2) followed by addition of 3.2 mL of THF, 0.6 mL of olefin solution (1:0.3 solution of α-cyclohexylstyrene and dodecane, 500:1 ratio of olefin substrate:Rh). Reaction mixture was headed for 18 hr at 90° C. under 300 psi of syn gas pressure. Conversion of α-cyclohexylstyrene to the desired 3-cyclohexyl-3-phenyl-propionaldehyde was 96.5% based on GC analysis. After cooling to room temperature reactor was opened and 0.25 mL of piperidine (1.2:1 ratio of piperidine:aldehyde substrate). After closing the reactor reaction mixture was headed for 18 hr at 90° C. under 300 psi of syn gas pressure. GC analysis showed formation of the desired amine, 1-(3-cyclohexyl-3-phenyl-propyl)-piperidine in 95% yield. The reaction mixture was taken out of the reactor and solvent was removed under reduced pressure leaving an oil. To this residue was added ~13 mL of acetonitrile, and the solution was heated using a heat gun. The solution was put into a freezer (−5° C.). After 2 days, the solution was decanted and the remaining light yellow oil was washed with cold acetonitrile (2×3 mL) and then dried under reduced pressure to give 150 mg of clean product. $^1H(C_6D_6)$: δ 0.65–1.66 (m, 17H), 1.83 (m, 1H), 1.92–2.31 (m, 7H), 2.36 (m, 1H), 7.04 (m, 3H), 7.13 (m, 2H). $^{13}C\{^1H\}$ and APT ($C_6D_6$): δ 25.30 ($CH_2$), 26.84 ($CH_2$), 27.09 ($CH_2$), 30.75 ($CH_2$), 31.58 ($CH_2$), 31.93 ($CH_2$), 43.79 (CH), 50.49 (CH), 55.09 ($CH_2$), 58.06 ($CH_2$), 126.09 (CH), 128.30 (CH), 128.86 (CH), 144.82 (C). GC-MS (m/e): 285.

D. Comparative Example: Hydroaminomethylation without Sequential Addition of Piperidine The reactor was charged with 0.085 mL of 0.05 M solution of $Rh(CO)_2(acac)$ and 0.085 mL of 0.11 M solution of tris(2-tert-butyl-4-methylphenyl)phosphite (ligand: Rh ratio of 2.2) followed by addition of 3.2 mL of THF, 0.6 mL of olefin solution (1:0.3 solution of α-cyclohexylstyrene and dodecane, 500:1 ratio of olefin substrate:Rh) and 0.25 mL of piperidine (1.2:1 ratio of piperidine:olefin substrate). Reaction mixture was headed for 18 hr at 90° C. under 300 psi of syn gas pressure. Conversion of α-cyclohexylstyrene was 11.7% based on GC analysis.

EXAMPLE 12

Preparation of Ibutilide

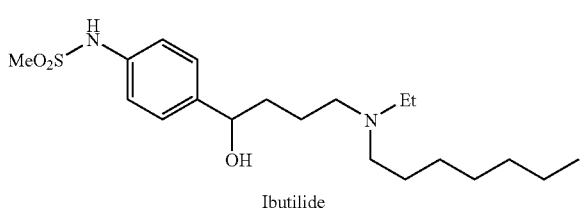

Ibutilide

A. Preparation of 4-Methanesulfonamido Benzaldehyde

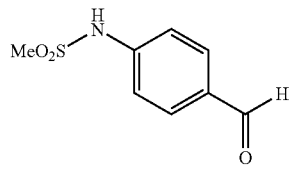

4-Methanesulfonamido Benzaldehyde

A solution of 4-nitrobenzaldehyde (6.60 g, 43.67 mmol) and p-toluenesulfonic acid monohydrate (153 mg, 0.804 mmol) were dissolved in 150 mL of toluene. Ethylene glycol (5 mL) was added, and the solution was refluxed with a Dean-Stark trap to azeotropically remove water. After 1 hour, the reaction was allowed to cool, whereupon 100 mL of diethyl ether was added. The solution was washed with twice with saturated $NaHCO_3$ solution and then with saturated NaCl solution. The solution was dried over $MgSO_4$ and evaporated to yield 4-nitrobenzaldehyde ethylene glycol acetal as a yellow solid (8.13 g, 95% yield).

$PtO_2$ (502 mg, 2.21 mmol) and $MgSO_4$ (7.34 g, 61.0 mmol) were added to a solution of 4-nitrobenzaldehyde ethylene glycol acetal (5.93 g, 30.4 mmol) in 60 mL of THF. The resulting suspension was stirred under 70 psi $H_2$ for 5 h. Solids were removed by filtration, and the filtrate was evaporated to give 4-aminobenzaldehyde ethylene glycol acetal as a golden liquid.

4-Aminobenzaldehyde ethylene glycol acetal (1.793 g, 10.86 mmol) was dissolved in 25 mL $CH_2Cl_2$ and cooled to 0° C. Pyridine was added (925 mg, 11.7 mmol), followed by dropwise addition of methanesulfonyl chloride (1.369 g, 11.9 mmol) over 30 min. The solution was allowed to warm to room temperature with stirring. After 16 h, 6 M NaOH (5 mL) was added followed by 150 mL of water. The aqueous layer was separated, washed with 50 mL $CH_2Cl_2$ and then acidified to pH 1 with 2 M HCl. The resulting suspension was extracted into ethyl acetate (4×50 mL) which was dried over $MgSO_4$ and evaporated to give 4-methanesulfonyl benzaldehyde as an orange solid (920 mg, 42% yield.

B. Preparation of 4-MeSO$_2$N(H)C$_6$H$_4$[C(H)(OH)(CH=CH$_2$)]

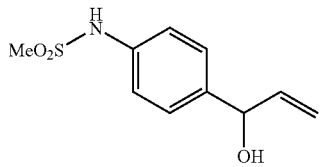

4-MeSO$_2$N(H)C$_6$H$_4$[C(H)(OH)(CH=CH$_2$)]

A solution of 4-methanesulfonyl benzaldehyde (834 mg, 4.19 mmol) in 13 mL of THF was added to 8.5 mL of 1.0 M (H$_2$C=CH$_2$)MgBr in THF. The resulting suspension was stirred for 3.5 h and then quenched with 10 mL of saturated NH$_4$Cl solution. The solution was extracted with diethyl ether (2×20 mL) and separated. The combined organic extracts were washed with water and saturated NaCl solution. After drying over MgSO$_4$, the solution was evaporated to give 4-MeSO$_2$N(H)C$_6$H$_4$[C(H)(OH)(CH=CH$_2$)] as an orange liquid (1.036 g).

C. Preparation of Ethyl-n-heptylamine

A solution of n-heptylamine (10.31 g, 89.4 mmol) in 100 mL CH$_2$Cl$_2$ was cooled in an ice bath. Pyridine (7.5 mL, 92.7 mmol) was added. Acetyl chloride (8.0 mL, 11 mmol) was gradually added over the course of 2 min. The ice bath was removed and the solution was allowed to warm to room temperature. After 1 h, water (100 mL) was added, and the organic layer was separated. The aqueous layer was extracted with 100 mL CH$_2$Cl$_2$. The combined organic extracts were washed with 10% aqueous HCl solution, saturated NaHCO$_3$ solution and then saturated NaCl solution. The solution was dried over MgSO$_4$ and evaporated to give n-heptyl acetamide as a colorless liquid (13.73 g, 98% yield).

A solution of n-heptyl acetamide (6.076 g, 38.63 mmol) in 6 mL of diethyl ether was added dropwise to a suspension on LiAlH$_4$ (4.60 g, 0.121 mol) in 150 mL diethyl ether. The suspension was refluxed for 8 h, cooled in ice and quenched with 4 mL H$_2$O, 4 mL of 2M NaOH and 12 mL of H$_2$O. The resulting suspension was filtered and the filtrate dried over Na$_2$SO$_4$. Evaporation of solvent gave (n-C$_7$H$_{15}$)N(H)C$_2$H$_5$ as a colorless liquid (5.29 g, 95% yield).

D. Preparation of Ibutilide

Rh(CO)$_2$(acac) (6.9 mg, 27 µmol) and Ligand 2 (25.0 mg, 29.8 µmol) were dissolved in 3 mL THF under nitrogen. The solution was transferred to a mechanically stirred autoclave and stirred under 400 psi (2760 kPa) of 1:1 H$_2$/CO for 30 min. A solution of 4-MeSO$_2$N(H)C$_6$H$_4$[C(H)(OH)(CH=CH$_2$)] (438 mg, 1.93 mmol) and (n-C$_7$H$_{15}$)N(H)C$_2$H$_5$ (283 mg, 1.97 mmol) in 3 mL of THF was was injected into the reactor against a flow of H$_2$/CO. The reactor was heated at 75° C. under 400 psi (2760 kPa) of 1:1 H$_2$/CO. After 18 h, the reactor was cooled to ambient temperature and vented. The reaction mixture was evaporated and redissolved in CH$_2$Cl$_2$ (20 mL). Product was extracted into 2 M NaOH (2×15 mL). The aqueous layer was then neutralized with 10% HCl and then extracted with CH$_2$Cl$_2$ (3×10 mL). The organic layer was dried in MgSO$_4$ and evaporated to give product as an orange liquid (410 mg). GC-MS indicated the product consisted of a mixture of Ibutilide and a branched isomer (linear:branched=25:1).

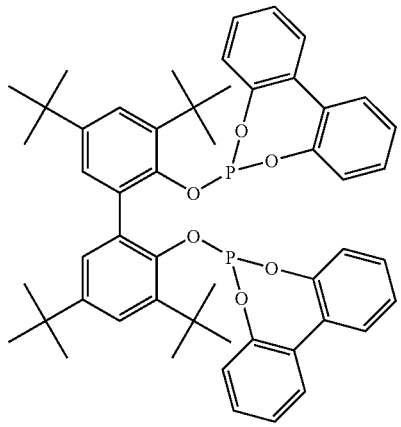

Ligand 2

EXAMPLE 13

Preparation of Aripiprazole

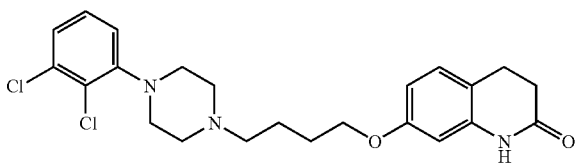

Rh(CO)$_2$(acac) (4.7 mg, 18 µmol) and Ligand 2 (19.7 mg, 23 µmol) were dissolved in 3 mL THF under nitrogen. The solution was transferred to a mechanically stirred autoclave and stirred under 400 psi (2760 kPa) of 1:1 H$_2$/CO for 30 min. A solution of 1-(2,3-dichlorophenyl)piperazine (616 mg, 2.66 mmol, which can be prepared according to the procedure of Morita, et al, *Tetrahedron* 1998, 54, 4811) and 7-(allyloxy)-3,4-dihydro-2(1H)-quinoline (547 mg, 2.69 mmol, which can be prepared according to the procedure described in WO 96/02508) in 7 mL of THF was injected into the reactor against a flow of H$_2$/CO. The reactor was heated at 75° C. under 400 psi (2760 kPa) of 1:1 H$_2$/CO. After 16 h, the reactor was cooled to ambient temperature and vented. The reaction mixture was evaporated and redissolved in 10 mL of CHCl$_3$. The solution was washed with 10% HCl solution, saturated NaHCO$_3$ solution and then saturated NaCl solution. After drying over MgSO4, the solution was evaporated to an orange oil.

EXAMPLE 14

Preparation of Terfenadine

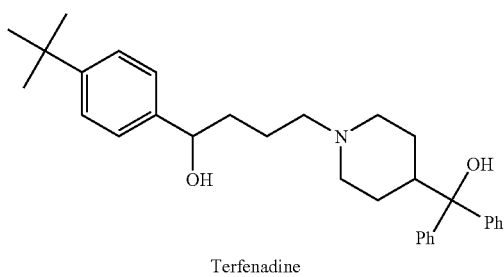

Terfenadine

A. Preparation of p-t-BuC$_6$H$_4$[C(H)(OH)(CH=CH$_2$)]

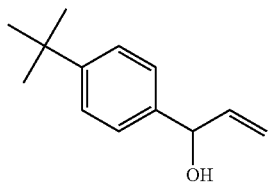

BrMg(vinyl) (1.0 M in THF, 38 mmol) was added dropwise to a solution of p-t-BuC$_6$H$_4$CHO (4.199 g, 25.88 mmol) in 15 mL THF under nitrogen. The solution was stirred at room temperature for 18 h and then refluxed for 2 h. Saturated aqueous NH$_4$Cl was added (50 mL) and the solution was extracted with diethyl ether (2×75 mL). The combined organic extracts were washed with saturated aqueous sodium chloride and dried over MgSO$_4$. The solution was evaporated to a yellow oil (5.24 g).

B. Preparation of Terfenadine

Rh(CO)$_2$(acac) (5.4 mg, 21 μmol) and Ligand 2 (23.9 mg, 28 μmol) were dissolved in 3 mL THF under nitrogen. The solution was transferred to a mechanically stirred autoclave and stirred under 250 psi of 1:1 H$_2$/CO for 2 h. A solution of p-t-BuC$_6$H$_4$[C(H)(OH)(CH=CH$_2$)] (676 mg, 3.55 mmol) and α,α-diphenyl-4-piperidinomethanol (950 mg, 3.55 mmol, commercially available from Acros) was prepared in 7 mL THF. The pressure was vented to the autoclave, and the substrate solution was injected into the reactor against a flow of 1:1 H$_2$/CO. The reactor was heated at 75° C. under 400 psi (2760 kPa) of 1:1 H$_2$/CO. After 18 h, the reactor was cooled to ambient temperature and vented. The reaction mixture was evaporated to yield 1.82 g of a viscous orange liquid which slowly crystallized upon standing.

EXAMPLE 15

Alternative Preparation of Terfenadine

A. Preparation of p-t-BuC$_6$H$_4$[C(H)(OSiMe$_3$)(CH=CH$_2$)]

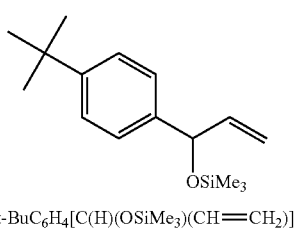

p-t-BuC$_6$H$_4$[C(H)(OSiMe$_3$)(CH=CH$_2$)]

Azidotrimethylsilane (5.0 μL, 37.7 mmol) was added under nitrogen to a solution of p-t-BuC$_6$H$_4$[C(H)(OH)(CH=CH$_2$)] (5.24 g, 27.54 mmol) in 5 mL anhydrous CH$_3$CN. The solution was stirred at ambient temperature for 3 days. Solvent was removed in vacuo to yield product as a yellow liquid (6.27 g, 23.9 mmol, 87% yield).

B. Synthesis of O-trimethylsilyl Terfenadine.

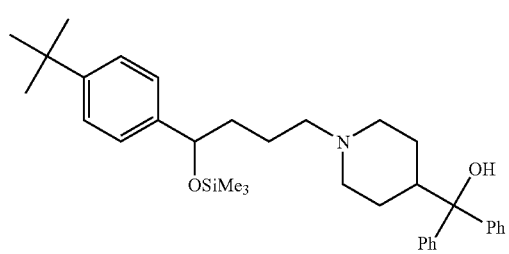

O-trimethylsilyl Terfenadine

Rh(CO)$_2$(acac) (9.3 mg, 36 μmol) and Ligand 2 (37.5 mg, 44.7 μmol) were dissolved in 3 mL THF under nitrogen. The solution was transferred to a mechanically stirred autoclave and stirred under 400 psi of 1:1 H$_2$/CO for 15 min. p-t-BuC$_6$H$_4$[C(H)(OSiMe$_3$)(CH=CH$_2$)] (1.212 g, 4.618 mmol) and α,α-diphenyl-4-piperidinomethanol (1.240 g, 4.638 mmol, available from Acros Organics) were dissolved in 10 mL THF. The pressure was vented to the autoclave, and the substrate solution was injected into the reactor against a flow of 1:1 H$_2$/CO. The reactor was heated at 75° C. under 400 psi (2760 kPa) of 1:1 H$_2$/CO. After 18 h, the reactor was cooled to ambient temperature and vented. The reaction mixture was evaporated to yield 2.29 g of a viscous orange liquid.

C. Synthesis of Terfenadine

The crude reaction product (2.29 g, 4.21 mmol) from B was dissolved in 20 mL of anhydrous THF. Solid [(PhCH$_2$)NMe$_3$]$^+$F$^-$ (870 mg, 1.20 equiv) was added, and the resulting suspension was stirred at ambient temperature for 3 days. Water was added, and the solution was extracted with diethyl ether (2×20 mL). The combined organic extracts were extracted with H$_2$O (10 mL) followed by brine (10 mL). The solution was dried over MgSO$_4$ and evaporated to give 2.146 g of a viscous orange liquid which slowly solidified to the desired product upon standing.

EXAMPLE 16

Preparation of Fexofenadine Methyl Ester

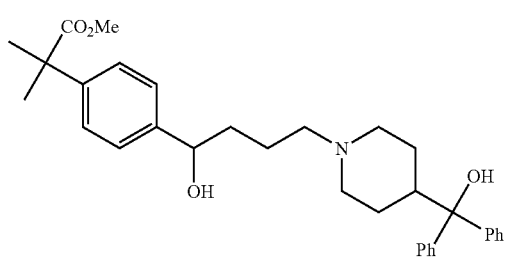

Fexofenadine Methyl Ester

A. Preparation of p-[Me$_2$(CO$_2$Me)C]C$_6$H$_4$CHO

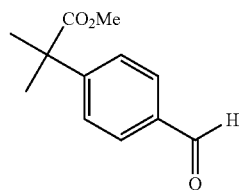

p-[Me$_2$(CO$_2$Me)C]C$_6$H$_4$CHO (p-(α-carbomethoxy-α'-methyl)ethylbenzaldehyde))

A solution of p-bromobenzaldehyde (15.4 g, 83.2 mmol) and p-toluenesulfonic acid monohydrate (200 mg, 1.05 mmol) was dissolved in 300 mL of toluene. Ethylene glycol (10 mL) was added, and the solution was refluxed with a Dean-Stark trap to azeotropically remove water. After 4 hours, 100 mL of ethyl acetate was added. The solution was washed with ice water, saturated NaHCO$_3$ solution and then with saturated NaCl solution. The solution was dried over MgSO$_4$ and evaporated to yield p-bromobenzaldehyde ethylene glycol acetal as a colorless oil which crystallized upon standing (18.02 g, 95% yield).

Lithium dicyclohexylamide (10.717 g, 57.23 mmol) was dissolved under nitrogen in 90 mL of toluene. Methyl isobutyrate (4.962 g, 48.60 mmol) was added and the resulting solution was stirred for 10 minutes. This solution was then added to solid p-bromobenzaldehyde ethylene glycol acetal (10.101 g, 44.09 mmol) and dipalladium tris(benzylideneacetone) (408 mg, 0.891 mmol Pd). Solid tri-t-butylphosphine (186.4 mg) was added and the resulting solution was stirred overnight. Dichloromethane (400 mL) and 5% HCl solution (400 mL) was added. The reaction mixture was filtered to remove a flocculent gray solid. The organic layer was separated, washed with 200 mL of 5% HCl solution, water (200 mL) and saturated sodium chloride solution. The resulting solution was evaporated in vacuo to give a yellow liquid that was dissolved in 150 mL of 2:1 acetone-H$_2$O. Pyridinium p-toluenesulfonate (478 mg) was added and the solution was stirred overnight. Acetone was removed by rotary evaporation, and product was extracted into diethyl ether. The solution was washed twice with 45 mL of water and then saturated sodium chloride solution. The solution was dried over MgSO$_4$ and evaporated to give product as a light yellow oil. Purification by column chromatography (silica gel, 9:1 hexane-EtOAc) gave the desired product as a pale yellow liquid (7.27 g, 80% yield).

B. Preparation of p-[Me$_2$(CO$_2$Me)C]C$_6$H$_4$[C(H)(OH)(CH=CH$_2$)]

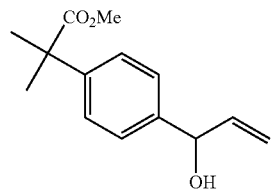

p-[Me$_2$(CO$_2$Me)C]C$_6$H$_4$[C(H)(OH)(CH=CH$_2$)]

BrMg(vinyl) (1.0 M in THF, 14 mmol) was added dropwise to a solution of p-t-BuC$_6$H$_4$CHO (2.896 g, 14.04 mmol) in 5 mL THF under nitrogen. The addition resulted in a large exotherm that caused the solution to boil. The solution was stirred at room temperature for 1.5 h. Saturated aqueous NH$_4$Cl was added (30 mL) and the solution was extracted with diethyl ether (2×50 mL). The combined organic extracts were washed with saturated aqueous sodium chloride and dried over MgSO$_4$. The solution was evaporated to the desired product as a yellow oil (5.24 g).

C. Preparation of Fexofenadine Methyl Ester

Rh(CO)$_2$(acac) (5.7 mg, 22 μmol) and Ligand 2 (23.5 mg, 28 μmol) were dissolved in 3 mL THF under nitrogen. The solution was transferred to a mechanically stirred autoclave and stirred under 250 psi of 1:1 H$_2$/CO for 1 h. A solution of p-[Me$_2$(CO$_2$Me)C]C$_6$H$_4$[C(H)(OH)(CH=CH$_2$)] (639 mg, 2.73 mmol) and α,α-diphenyl-4-piperidinomethanol (730 mg, 2.73 mmol) was prepared in 10 mL THF. The pressure was vented to the autoclave, and the substrate solution was injected into the reactor against a flow of 1:1 H$_2$/CO. The reactor was heated at 75° C. under 400 psi (2760 kPa) of 1:1 H$_2$/CO. After 18 h, the reactor was cooled to ambient temperature and vented. The reaction mixture was evaporated to yield 1.49 g of the desired product as an orange foamy solid.

What is claimed is:

1. A method comprising the step of contacting under hydroaminomethylation conditions a) an olefin; b) a primary or secondary amine or ammonia; c) a neutral rhodium-monodentate phosphite ligand complex which is prepared by contacting a neutral rhodium procatalyst with a monodentate phosphite ligand and is further characterized in that no strong acid is formed from reaction of the complex with the syngas and d) syngas.

2. A method comprising the step of contacting under hydroaminomethylation conditions a) an olefin; b) a primary or secondary amine or ammonia; c) a neutral rhodium-monodentate phosphite ligand complex prepared by contacting a neutral rhodium procatalyst selected from the group consisting of [Rh(CO)$_2$(acac)], [Rh$_4$(CO)$_{12}$], [Rh$_2$(OAc)$_4$], [Rh(C$_2$H$_4$)$_2$(acac)], [Rh(cyclooctadiene)(acac)], and [Rh(acac)$_3$] with a monodentate phosphite ligand.

3. The method of claim 1 wherein the olefin is selected from the group consisting of cyclohexene, oleic acid diethanolamide, a terminally unsaturated isopolypropylene, ethylidene norbornene, polybutadiene, styrene, α-cyclohexylstyrene and tetrahydrobenzaldehyde, and the amine or ammonia is selected from the group consisting of dimethylamine, N,N'-dimethylpropylenediamine, morpholine, piperidine, diethanolamine, dibenzylamine and ammonia.

4. The method of claim 1 wherein the monodentate phosphite ligand is selected from the group consisting of triphenylphosphite, tri(2,4-di-t-butylphenyl)phosphite, tri-o-tolylphosphite, tri-p-tolyiphosphite, trimethyiphosphite, triethyiphosphite, tn-n-propyiphosphite, tri-n-butylphosphite, tri-t-butylphosphite, tri-1-naphthylphosphite, tri-2-naphthylphosphite, 2,2'-biphenolphenylphosphite, 2,2',4,4'-tetra-t-butyl-2,2'-biphenol 2,4-di-t-butylphenylphosphite, and tribenzylphosphite.

5. The method of claim 1 wherein the primary or secondary amine or ammonia is either added at the beginning of the reaction or is added sequentially, after conversion of the olefin to the intermediate product of hydroformylation.

6. The method of claim 5 where the olefin is 1,1'-disubstituted and the primary or secondary amine or ammonia is added sequentially, after conversion of the olefin to the intermediate product of hydroformylation.

7. A method comprising the step of contacting under hydroaminomethylation conditions a) an olefin of the class $ArXCR{=}CR_2$; b) a secondary amine; c) a rhodium-phosphorous ligand complex; and d) syngas; wherein Ar is aryl or substituted aryl, each R is independently hydrogen, alkyl, cycloalkyl, aryl, aralkyl, substituted alkyl, substituted cycloalkyl, substituted aryl, or a heteroatom containing group, and X is a linking group, and the phosphorous ligand is polydentate with the proviso that when X is —$CH_2$— or —$OCH_2$—, the phosphorous ligand is a phosphite ligand.

8. The method of claim 7 wherein Ar is substituted phenyl, and X is hydroxymethylene.

9. The method of claim 8 wherein Ar is p- Y -phenyl or methanesulfonamidophenyl where Y is $C(CH_3)_2R''$ wherein R" is methyl, cyano, hydroxymethylene, alkoxymethylene, carbohydroxy, carbomethoxy, carboethoxy, carbobenzyloxy, amido, orthoformate, formyl, 2-oxazoline, or 2-benzoxazole.

10. The method of claim 8 wherein Ar is p-t-butylphenyl, p-methanesulfonamidophenyl, or p-(α-carbomethoxy-α'-methyl)ethylphenyl.

11. The method of claim 10 wherein the amine α,α-diphenyl-4-piperidino methanol.

12. The method of claim 11 wherein the phosphorous ligand is a phosphite.

13. A method comprising the step of contacting under hydroaminomethylation conditions a) an olefin of the class $ArXCR{=}CR_2$ wherein Ar is p-t-butvlphenvl, p-methanesulfonamidophenyl, or p-(α-carbomethoxv-α'-methyl) ethylphenyl; b) α,α-diphenyl-4-piperidino methanol; c) a rhodium-phosphorous ligand complex; and d) syngas; wherein the phosphorous ligand is represented by the following structure:

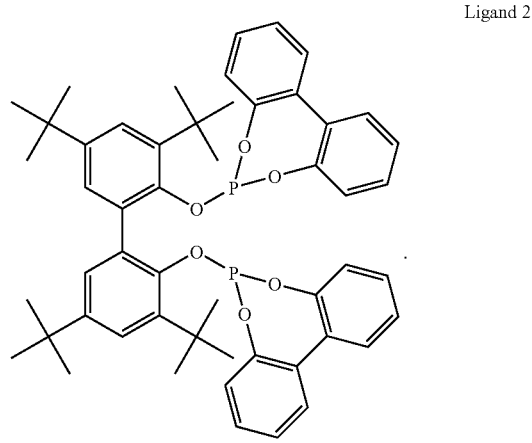

Ligand 2

14. The method of claim 7 where the ligand is bidentate.

* * * * *